(12) United States Patent
Berna et al.

(10) Patent No.: US 6,958,233 B2
(45) Date of Patent: Oct. 25, 2005

(54) PROCESS FOR THE PREPARATION OF PHARMACEUTICALLY ACCEPTABLE SALTS OF (R,S)-S-ADENOSYL-L-METHIONINE

(75) Inventors: Marco Berna, Monza (IT); Lino Sivieri, Monza (IT); Gianni Santambrogio, Monza (IT); Ermanno Valoti, Monza (IT)

(73) Assignee: Chementecno S.r.l., Monza (IT)

(*) Notice: Subject to any disclaimer, the term of this patent is extended or adjusted under 35 U.S.C. 154(b) by 429 days.

(21) Appl. No.: 10/142,876

(22) Filed: May 13, 2002

(65) Prior Publication Data

US 2002/0173012 A1 Nov. 21, 2002

Related U.S. Application Data

(62) Division of application No. 09/829,906, filed on Apr. 11, 2001, now abandoned.

(30) Foreign Application Priority Data

May 25, 2000 (IT) ..................................... MI2000A1158

(51) Int. Cl.[7] .............................................. C12P 41/00
(52) U.S. Cl. ..................................................... 435/280
(58) Field of Search ........................................ 435/280

(56) References Cited

U.S. PATENT DOCUMENTS 3,954,726 A 5/1976 Fiecchi
4,621,056 A 11/1986 Gennari

FOREIGN PATENT DOCUMENTS

FR 2 531 714 2/1984

OTHER PUBLICATIONS

Caonline Registry citation of S–adenosyl–L–methionine and chemical structure.*
WordIQ.com definition of Room and Ambient Temperature.*
J.L. Hoffman, "Chromatographic analysis of the chiral and covalent instability of S–adeosyl–L–methionine" BIO-CHEMISTRY, vol. 25, 1986, pp. 4444–4449.
Mark L. Stolowitz and M.J. Minch, S–Adenosyl–L–methionine and S–Adenosyl–L–homocysteine, and NMR Study[1], Received Apr. 13, 1981, pp. 6015–6019.
John Warcup Cornforth, [1a,b] Scott A. Reichard, 1[c] Paul Talalay, [1,c] H. L. Carrell, [1d] and Jenny P. Glusker [1d], Determination of the Absolute Configuration at the Sulfonium Center of S–Adenosylmethionine. Correlation with the Absolute Configuration of the Diasteromeric S–Carrboxymethyl–(S)–methionine Salts, Received Apr. 25, 1977, pp. 7292–7300.
Creason et al., "Soybeans andRadish Leaves Contain Only One of the Sulfonium Diasteroisomers of S–Adenosylmethionine", Phytochemistry 24 (6) : 1151–1155 (1985).
Matos et al., "S–Adenosylmethionine: Stability and Stabilization", Bioorganic Chemistry 15: 71–80 (1987).

* cited by examiner

Primary Examiner—Sandra E. Saucier
(74) Attorney, Agent, or Firm—Oblon, Spivak, McClelland, Maier & Neustadt, P.C.

(57) ABSTRACT

The present invention relates to a process for the preparation of pharmaceutically acceptable salts of (R,S)-S-adenosyl-L-methionine and allows to obtain the salified (R)-(+)-S-adenosyl-L-methionine diasteroisomer in amounts lower than or equal to 3% with respect to the salified (S)-(+)-S-adenosyl-L-methionine diastereoisomer; the salts that can be obtained by the process of the invention keep their configuration stable in time.

9 Claims, No Drawings

PROCESS FOR THE PREPARATION OF PHARMACEUTICALLY ACCEPTABLE SALTS OF (R,S)-S-ADENOSYL-L-METHIONINE

This application is a division of application Ser. No. 09/829,906 filed on Apr. 11, 2001, now abandoned.

BACKGROUND OF THE INVENTION

1. Field of the Invention

The present invention relates to a process for the preparation of pharmaceutically acceptable salts of (R,S)-S-adenosyl-L-methionine (hereinafter referred to as (R,S)-SAMe). ("(R,S)-S-adenosyl-L-methionine" means a mixture of (R)-S-adenosyl-L-methionine and (S)-S-adenosyl-L-methionine.)

In particular, the invention relates to a process for the preparation of pharmaceutically acceptable salts of (R,S)-SAMe, wherein the salified (R)-(+)-S-adenosyl-L-methionine diastereoisomer (hereinafter referred to as (R)-(+)-SAMe) is produced in amounts lower than or equal to 3% with respect to the salified (S)-(+)-S-adenosyl-L-methionine diastereoisomer (hereinafter referred to as (S)-(+)-SAMe.

2. Description of the Background

As it is known, (R,S)-SAMe is a physiological methyl donor involved in enzymatic transmethylation reactions, that is present in all living organisms and has therapeutical effects on chronic hepatic diseases, adiposis, lipaemia, atherosclerosis and it is desirable, therefore, to produce it in high amounts.

It is also known, (J. W. Comforth, J.A.C.S., 1977, 99, 7292–7300; Stolowitz et al., J.A.C.S., 1981, 103, 6015–6019) that the products containing (R,S)-SAMe consist of a mixture of two diastereoisomers: (R)-(+)-SAMe and (S)-(+)-SAMe, having the following structural formulae:

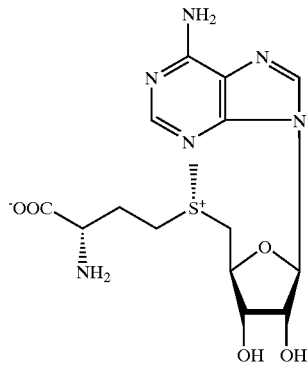

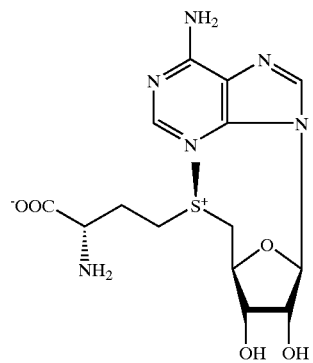

Moreover, it was demonstrated (De La Haba et al., J.A.C.S., 1959, 81, 3975–3980) that only one of the two diastereoisomers, i.e. (S)-(+)-SAMe, is enzymatically active for the transmethylation and spontaneously racemises, thereby giving rise to the formation of the inactive diastereoisomer (R)-(+)-SAMe in a percentage equal to about 20% (Wu et al., Biochemistry 1983, 22, 2828–2832).

The Applicant, in fact, has noted that in all the commercially available-products based on (R,S)-SAMe, the inactive diastereoisomer (R)-(+)-SAMe is present in percentages equal to at least 20%; it was also noted that said percentages increase in time even up to 40% and more.

This observation clearly confirms that the diasteroisomer mixture is unstable in time, which, on the other side, had already been noted in relation with the product in solution (G. L. Creason et al., Phytochemistry, vol. 24, N. 6, 1151–1155, 1985; H. C. Uzar, Liebigs Ann. Chem. 1989, 607–610).

The demand for (R,S)-SAMe derivatives wherein the percentage of the active (S)-(+)-SAMe diastereoisomer is clearly higher with respect to the inactive (R)-(+)-SAMe isomer and wherein said percentage turns out to be stable in time, is particularly felt in the field.

It was also found that there is an obstacle to the use of (R,S)-SAMe and the pharmaceutically acceptable salts thereof at the industrial level because of their thermal instability, even at room temperature, and of the complexity of the preparation and purification processes thereof.

Several processes for the purification of (R,S)-SAMe and for the production of the pharmaceutically acceptable salts thereof are known.

However, the known purification processes, besides providing the use of strong acid resins (JP 13680/1971) or chelate-type resins (JP 20998/1978) or particular and expensive reactants, such as picric or picolinic acid (U.S. Pat. Nos. 3,707,536 and 3,954,726), bring anyhow to the partial racemisation of the sulphur chiral center of (R,S)-SAMe and, therefore, lead to final products containing the inactive diastereoisomer in amounts higher than 20%.

Purification processes that use weak acid resins are also known (JP 14299/1981, FR-A-2531714, EP-A-0141914), which allow, however, to obtain just a partial separation of (SS, RS)-SAMe and, therefore, an insufficient purity degree for pharmaceutical purposes.

Even if the realization of some of the above-identified processes enables to obtain a higher purity, the partial racemization implies, at any event, that at least 20% of the inactive diastereoisomer should be present; in some cases moreover (FR-2531714), in order to extract the product from the cells, there is provided the use of potassium bicarbonate, with subsequent precipitation of potassium perchlorate, which brings about problems firstly in the separation and then in the disposal of the product. In EP-A-0141914, the lysis of the cells of the yeast containing (R,S)-SAMe is carried out in the presence of an organic solvent (for example, ethyl acetate, acetone, etc.) by using, moreover, chromatographic columns based on 100–200 mesh resins, with high investment and maintaining costs. The use of solvents for the extraction of (R,S)-SAMe necessarily implies the employment of antideflagrant plants and a recovery, distillation and solvent recovery systems, besides the necessary drying of the exhausted mycelium, in order to avoid that it is discharged with the residual solvent, all these factors clearly bringing about additional investment and operation costs.

DESCRIPTION OF THE INVENTION

According to a first aspect, the present invention relates to a process for the preparation of pharmaceutically acceptable salts of (R,S)-SAMe, wherein the salified (R)-(+)-SAMe diastereoisomer is present in amounts lower than or equal to 3% with respect to the salified (S)-(+)-SAMe diastereoisomer, which, at a temperature higher than or equal to 0–12° C., comprises:

the purification of (R,S)-S-adenosyl-L-methionine from enriched yeast, which shall contain at least 6 g/l thereof, which comprises:
(a)—the adjustment of the pH value to 1.2–3.5;
(b)—the preparation of an aqueous lysate of (R,S)-SAMe from the enriched yeast;
(c)—the microfiltration of the resulting lysate;
(d)—the absorption of the resulting microfiltrate on a weak acid resin, by eluting with a 0.1–2 N inorganic acid solution;
(e)—the decolouration of the resulting eluate;
the concentration of the decolourised eluate, by reverse osmosis, from 30 to 70% by volume;
the addition of stoichiometric amounts of at least one pharmaceutically acceptable acid salt to the concentrated eluate, so as to obtain the corresponding pharmaceutically acceptable salt of (R,S)-SAMe.

According to a preferred aspect, the so obtained pharmaceutically acceptable salt of (R,S)-SAMe can be subjected to lyophilization.

According to another preferred aspect, the process of the invention is carried out at a temperature of 2–5° C.

According to a further preferred aspect, the pH value in step (a) is 1–2, whereas the preparation of the lysate in step (b) can take place by passing the yeast through a breaking-cells equipment, then proceeding with the microfiltration of the so obtained yeast, for example on a ceramic membrane.

The enriched yeast on which (R,S)-SAMe is purified preferably contains at least 8–10 g/l of (R,S)-SAMe; the pharmaceutically acceptable acid is selected, preferably, from sulphuric acid and paratoluensulphonic acid.

It can be noted that the process of the invention allows to use resin/product ratios equal to, for example, 10–20 liters of resin pro kg of absorbed product, which are advantageous with respect to what has been disclosed in JP 20998/1978.

The process of the invention allows to produce salts of (R,S)-SAMe wherein, even at room temperature, it is possible to detect a percentage of the (S)-(+)-SAMe diastereoisomer equal to at least 97 with respect to the (R)-(+)-SAMe diastereoisomer which is present, accordingly, in percentages lower than or equal to 3.

The process of the invention allows moreover to exclude the use of organic solvents in the preparation of the lysate, with remarkable advantages with respect to the purification steps of the pharmaceutically acceptable salts of (R,S)-SAMe, as well as ecological and environmental advantages.

It is furthermore possible to obtain a higher yield and purity of the pharmaceutically acceptable salts of (R,S)-SAMe with respect to those obtainable by known processes; a purity equal to at least 98% in (R,S)-SAMe and a yield equal to at least 90 are obtained, in fact, with respect to the fermented product.

Thanks to its particular conditions, the process of the invention allows to avoid the degradation of (R,S)SAMe during the preparation of the lysate and allows to obtain a lysis with a yield higher than 98% and with a content of by-products, the main product of which being 5-deacyl-5-methylthioadenosine, lower than 1%.

(R,S)-SAMe, suitably salified as above described, can be produced, for example, by fermenting a suitable microorganism, such as *Saccharomyces pastorianus* (ex *Saccharomyces carlsbergensis* CBS 1513), *Saccharomyces cerevisiae* (IFO 2044), *Torulopsis utilis* and *Candida utilis*.

The yeast containing (R,S)-SAMe can be enriched by the processes known in the field, such as for example, the Schlenk method described in "Journal of Biological Chemistry", vol. 29, page 1037, (1987), which was modified only in optimizing the use of DL methionine and which was conducted at a maximum temperature of 27.5° C. for about 20 hours.

The (R,S)-SAMe-enriched yeast (which, in order to be advantageously employed in the realization of the present invention, indicatively contains at least 6 g/l of (R,S)-SAMe, undergoes, upon adjustment of the pH value to 1.2–3.5, a cellular lysis process, by passing the yeast, preferably, through a cell-breaking equipment.

The resulting lysate, after being subjected to microfiltration, for example on a ceramic membrane such as Kerasep® K09A, is adsorbed on a weak acid carboxylic resin, preferably of the cationic type, such as Rohm and Haas® IRC86, preferably until saturation (about 150 g/l), and eluted with a solution of an inorganic acid such as, for example, 0.1–2 N sulphuric acid, hydrochloric acid, etc.

The decolouration of the resulting eluate takes then place, for example by means of a copolymer resin with a styrene-divinylbenzene unit, such as Resindion® 825L.

The resulting eluate containing (R,S)-SAMe is concentrated, by reverse osmosis, from 30 to 70%, preferably from 40 to 50% by volume. The so obtained concentrate is added with stoichiometrically equivalent amounts of an acid or a mixture of pharmaceutically acceptable acids, such as those indicated above. The so obtained products can be used for possible preparations in solution or can be subjected to lyophilisation, when one wishes to use them in the solid form.

The following examples illustrate the invention without limiting it.

EXAMPLE 1

1000 kg of yeast obtained by fermentation of *Saccharomyces carlsbergensis* were enriched with (R,S)-SAMe according to the Schlenk method, modified as follows. The yeast was added with 100 kg of yeast cream (which, upon dilution with 100 l of deionised water has a 2.2 g/l titer), 2 kg of DL methionine, 12 kg of hydrated glucose and 1.5 kg of citric acid, keeping under stirring at 27° C.+0.5° C. for 22 hours, aerating through emission of sterile filtered air at a flow of 0.6 l/l/m, thereby obtaining 9 g/l of (R,S)-SAMe.

After adjusting pH at 1.2 by means of $H_2SO_4$, lysis was carried out, at a temperature of 12° C., by the "Constant Cell Disruption System" produced by Constant System Ltd., a pressure-type cell-breaking system with a cooling system. The solution was then cooled by using first cold water and then brine, until the solution was brought to a temperature of about 2° C.

The obtained mixture was then conveyed to a microfitration plant, endowed with cartridges of the type Verind A-10 HFM 180 SM, for separating the exhausted solid from the enriched liquid. The panel was washed with 2000 l of demineralised water at 2° C. The filtration yield was 98%.

The enriched solution was passed through the IRC 86 resin (Rohm and Haas®), a carboxylic resin and eluted with 1 N sulphuric acid, still keeping the temperature at about 2° C.

The collected eluate was decoulorised by using a Resindion® 825L resin. The enriched solution was concentrated by reverse osmosis until a 40% concentration of (R,S)-SAMe was obtained. Corresponding stoichiometric amounts of sulphuric acid and paratoluensulphonic acid were then added to give the disulphate paratoluensulphonate of (R,S)-SAMe. The final yield of (R,S)-SAMe disulphate paratoluensulphate was 90%.

The content of (R)-(+)-SAMe disulphate paratoluensulphonate in the diastereoisomer mixture of (R,S)-SAMe disulphate paratoluensulphonate, analyzed by HPLC, turned out to be 1%. The relevant data are reported in the following, in the table concerning sample N. 4.

EXAMPLE 2

1000 kg of yeast, obtained by fermentation of *Saccharomyces carlsbergensis* enriched with (R,S)-SAMe according to the method described in EXAMPLE 1, with an activity equal to 8.2 g/kg, were lysated by a cell-breaking system at a temperature of 12° C. and at a 2 pH. After adding 500 l of water to the resulting solution, the microfiltration and the subsequent steps were carried out, analogously to what described in EXAMPLE 1, washing with 2000 l of cold demineralized water (about 5° C.). 7.5 kA of (R,S)-SAMe were obtained which, after being concentrated by reverse osmosis, were salified obtaining a 91.4% yield of (SS, RS)-SAMe disulphate paratoluensulphonate (lysis yield: 99%; purification yield: 98%). The time elapsing from the end of the fermentation to the concentration by reverse osmosis was 32 hours. The relevant data are reported in the following, in the table concerning sample N. 5.

EXAMPLE 3

The solution obtained by the process of EXAMPLE 1, after absorption on IRC 86 (Rohm and Haas®) resin, was eluted with 1 N sulphuric acid.

The obtained solution was concentrated up to 20% and then added with sulphuric acid and paratoluensulphonic acid in a stoichiometric amount, thereafter it was further concentrated until a 40% solution was obtained. 14.09 kg of (R,S)-SAMe disulphate paratoluensulphonate were obtained, with a transformation yield of 97.8%. The relevant data are reported in the following, in the table relating to sample N. 6.

EXAMPLE 4

Comparative 3 samples of SAMIR® [(R,S)-SAMe], produced by Knoll Farmaceutici S.p.A., were analyzed by HPLC. The values measured for each sample are as follows:

SAMPLE 1—100 mg of SAMIR® (vials) batch 045-021; expiration date 06/2000.

| peak No. | retention time | peak area | peak height | area | height (%) |
|---|---|---|---|---|---|
| 1 | 3.661 | 0.26322 | 0.00171 | 0.286 | 0.410 |
| 2 | 4.246 | 0.33608 | 0.00210 | 0.365 | 0.503 |
| 3 | 4.591 | 1.82467 | 0.00906 | 1.984 | 2.166 |
| 4 | 5.429 | 1.00324 | 0.00573 | 1.090 | 1.370 |
| 5 | 5.888 | 51.25485 | 0.25301 | 55.715 | 60.500 |
| 6 | 6.206 | 37.31255 | 0.14658 | 40.560 | 35.051 |

Peak No. 5, corresponding to (S)-(+)-SAMe, indicates a percentage of 58%, whereas peak No. 6, corresponding to (R)-(+)-SAMe, indicates a percentage of 42%.

SAMPLE 2—200 mg of SAMIR® (tablets); batch 121; expiration date 05/2002.

| peak No. | retention time | peak area | peak height | area (%) | height (%) |
|---|---|---|---|---|---|
| 1 | 3.665 | 0.35979 | 0.00221 | 0.194 | 0.269 |
| 2 | 4.238 | 0.40764 | 0.00265 | 0.220 | 0.322 |
| 3 | 4.538 | 3.58281 | 0.01624 | 1.932 | 1.973 |
| 4 | 5.411 | 1.60136 | 0.00919 | 0.863 | 1.116 |
| 5 | 5.828 | 108.11943 | 0.52553 | 58.299 | 63.833 |
| 6 | 6.144 | 71.38583 | 0.26746 | 38.492 | 32.487 |

Peak No. 5, corresponding to (S)-(+)-SAMe, indicates a percentage of 60%, whereas pea No. 6, corresponding to (R)-(+)-SAMe, indicates a percentage of 40%.

SAMPLE 3—400 mg of SAMIR® (tablets); batch 040; expiration date 10/2002.

| Peak No. | retention time | peak area | peak height | area (%) | height (%) |
|---|---|---|---|---|---|
| 1 | 3.386 | 0.03675 | 0.00041 | 0.010 | 0.027 |
| 2 | 5.419 | 1.40489 | 0.00853 | 0.387 | 0.559 |
| 3 | 5.785 | 214.15843 | 0.99534 | 58.973 | 65.233 |
| 4 | 6.092 | 147.47305 | 0.52125 | 40.610 | 34.162 |
| 5 | 13.468 | 0.07286 | 0.00029 | 0.020 | 0.019 |

Peak No. 3, corresponding to (S)-(+)-SAMe, indicates a percentage of 59%, whereas peak No. 4, corresponding to (R)-(+)-SAMe, indicates a percentage of 41%.

EXAMPLE 5

The products obtained according to the process of the invention in EXAMPLES 1–3, samples 4–6 respectively, were analyzed, similarly to what has been described in example 4, after four months from the date of their production.

The measured values for each sample were as follows:
SAMPLE 4 (EXAMPLE 1); batch 003/R.

| peak No. | retention time | peak area | peak height | area (%) | height (%) |
|---|---|---|---|---|---|
| 1 | 2.595 | 10.89547 | 0.06085 | 4.340 | 4.566 |
| 2 | 2.735 | 7.93823 | 0.07825 | 3.163 | 5.873 |
| 3 | 2.834 | 8.13165 | 0.08741 | 3.239 | 6.561 |
| 4 | 2.946 | 20.91077 | 0.12978 | 8.331 | 9.740 |
| 5 | 3.355 | 5.91998 | 0.02933 | 2.358 | 2.201 |
| 6 | 3.651 | 1.91541 | 0.00909 | 0.763 | 0.683 |
| 7 | 4.136 | 192.60315 | 0.92893 | 76.728 | 69.716 |
| 8 | 4.958 | 1.81995 | 0.00603 | 0.725 | 0.453 |
| 9 | 6.423 | 0.88589 | 0.00276 | 0.353 | 0.207 |

Peak No. 7, corresponding to (S)-(+)-SAMe, indicates a percentage of 99%, whereas peak No. 8, corresponding to (R)-(+)-SAMe, indicates a percentage of 1%.

SAMPLE 5 (Example 2); KF=2.3%; titre=102.6%; batch 001/R.

| peak No. | retention time | peak area | peak height | area (%) | height (%) |
|---|---|---|---|---|---|
| 1 | 2.588 | 0.23402 | 0.00223 | 0.075 | 0.155 |
| 2 | 2.817 | 0.08934 | 0.00099 | 0.029 | 0.068 |
| 3 | 2.908 | 0.28759 | 0.00228 | 0.092 | 0.158 |
| 4 | 3.082 | 6.84701 | 0.04649 | 2.194 | 3.227 |
| 5 | 3.388 | 0.69924 | 0.00391 | 0.224 | 0.272 |
| 6 | 3.697 | 0.84270 | 0.00466 | 0.270 | 0.323 |
| 7 | 4.224 | 295.93649 | 1.35851 | 94.844 | 94.306 |
| 8 | 5.153 | 5.50257 | 0.01712 | 1.763 | 1.188 |
| 9 | 6.696 | 1.58749 | 0.00436 | 0.509 | 0.303 |

Peak No. 7 corresponding to (S)-(+)-SAMe, indicates a percentage of 98%, whereas peak No. 8, corresponding to (R)-(+)-SAMe, indicates a percentage of 2%.

SAMPLE 6 (EXAMPLE 3); KF=1.39%; titre=102.7; batch 004/R.

| peak No. | retention time | peak area | peak height | area (%) | height (%) |
|---|---|---|---|---|---|
| 1 | 2.584 | 0.19250 | 0.00169 | 0.058 | 0.109 |
| 2 | 2.825 | 0.13395 | 0.00135 | 0.041 | 0.088 |
| 3 | 2.894 | 0.22074 | 0.00196 | 0.067 | 0.127 |
| 4 | 3.060 | 6.91884 | 0.04741 | 2.094 | 3.072 |
| 5 | 3.355 | 0.82868 | 0.00484 | 0.251 | 0.314 |
| 6 | 3.661 | 1.53681 | 0.00907 | 0.465 | 0.588 |
| 7 | 4.162 | 313.00031 | 1.45354 | 94.736 | 94.209 |
| 8 | 5.026 | 5.89462 | 0.01854 | 1.784 | 1.201 |
| 9 | 6.528 | 1.66553 | 0.00450 | 0.504 | 0.292 |

Peak No. 7, corresponding to (S)-(+)-SAMe, indicates a percentage of 98%, whereas peak No. 6, corresponding to (R)-(+)-SAMe, indicates a percentage of 2%.

What is claimed is:

1. A process for the preparation of a pharmaceutically acceptable salt of a mixture of (R)-S-adenosyl-L-methionine and (S)-S-adenosyl-L-methionine from enriched yeast containing at least 6 g/kg of (R)-S-adenosyl-L-methionine and (S)-S-adenosyl-L-methionine, wherein the process is performed at a temperature of 0–12° C., comprising:

(a) adjusting the yeast to a pH of 1.0 to 3.5, (b) lysing the yeast to produce a lysate, (c) microfiltrating the lysate to produce a microfiltrate, (d) adsorbing the microfiltrate on a weak acid resin and eluting with 0.1–2 N inorganic acid to produce an eluate, (e) decolorizing the eluate to produce a decolorized eluate, (f) concentrating the decolorized eluate by reverse osmosis to 30–70% by volume to produce a concentrated, decolorized eluate, (g) adding stoichiometric amounts of a pharmaceutically acceptable acid to the concentrated, decolorized eluate to produce a pharmaceutically acceptable salt of the mixture of (R)-S-adenosyl-L-methionine and (S)-S-adenosyl-L-methionine, wherein the salified (R)-S-adenosyl-L-methionine is present in amounts lower than or equal to 3% with respect to the (S)-S-adenosyl-L-methionine.

2. Process according to claim 1, wherein the pharmaceutically acceptable salt of the mixture of (R)-S-adenosyl-L-methionine and (S)-S-adenosyl-L-methionine is subjected to lyophilization.

3. Process according to claim 2, wherein the pH value in step (a) is 1–2.

4. Process according to claim 1, wherein the pH value in step (a) is 1–2.

5. Process according to claim 1, wherein the preparation of the lysate in step (b) takes place by passing the yeast through a cell-breaking equipment.

6. Process according to claim 1, wherein the temperature is 2–5° C.

7. Process according to claim 1, wherein the enriched yeast contains at least 8–10 g/kg of the mixture of (R)-S-adenosyl-L-methionine and (S)-S-adenosyl-L-methionine.

8. Process according to claim 1, wherein the pharmaceutically acceptable acid is selected from sulphuric acid and paratoluensulphonic acid.

9. Process according to claim 1, wherein step (b) is carried out in the absence of organic solvents.

* * * * *